(12) United States Patent
Zhao et al.

(10) Patent No.: US 10,502,358 B2
(45) Date of Patent: Dec. 10, 2019

(54) LOCK DEVICES AND SUPPORT ARMS THEREOF AND ULTRASOUND IMAGING SYSTEMS USING THE SAME

(71) Applicant: SHENZHEN MINDRAY BIO-MEDICAL ELECTRONICS CO., LTD., Shenzhen (CN)

(72) Inventors: Yanqun Zhao, Shenzhen (CN); Zhiwu Chen, Shenzhen (CN); Dongsheng Liang, Shenzhen (CN); Dahui Zhu, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 1175 days.

(21) Appl. No.: 14/624,378

(22) Filed: Feb. 17, 2015

(65) Prior Publication Data

US 2015/0308610 A1   Oct. 29, 2015

Related U.S. Application Data

(63) Continuation of application No. PCT/CN2013/074489, filed on Apr. 22, 2013.

(30) Foreign Application Priority Data

Aug. 17, 2012 (CN) .......................... 2012 1 0294550

(51) Int. Cl.
  *A61B 8/14* (2006.01)
  *F16M 11/18* (2006.01)
  (Continued)

(52) U.S. Cl.
  CPC ............. *F16M 11/18* (2013.01); *A47B 21/02* (2013.01); *A47B 21/0314* (2013.01);
  (Continued)

(58) Field of Classification Search
  None
  See application file for complete search history.

(56) References Cited

U.S. PATENT DOCUMENTS

| 6,672,553 B1 | 1/2004 | Lin | |
| 2010/0313777 A1* | 12/2010 | Aoki | B41F 21/10 |
| | | | 101/409 |
| 2011/0174937 A1* | 7/2011 | Sullivan | F16M 11/10 |
| | | | 248/122.1 |

FOREIGN PATENT DOCUMENTS

| CN | 2177153 Y | 9/1994 |
| CN | 201103779 Y | 8/2008 |
| CN | 201198855 Y | 2/2009 |

* cited by examiner

*Primary Examiner* — Joel F Brutus
(74) *Attorney, Agent, or Firm* — Kory D. Christensen

(57) ABSTRACT

A lock device is disclosed, which includes: a holder which is provided with a through hole running through the holder and a slide intersecting with the through hole; a guide bar, which is provided with an outer threaded area on at least a portion of a surface and passes through the through hole, and the outer threaded area is located where the through hole intersects with the slide; a lock component received in the slide, and the end of the lock component facing toward the guide bar is provided with a lock threaded area which can engage with the outer threaded area of the guide bar; and a drive assembly which drives a lock assembly to move toward or away from the guide bar in the slide. The guide bar is locked when threads on the lock threaded area engage with outer threads on the outer threaded area.

19 Claims, 6 Drawing Sheets

(51) Int. Cl.
*A61B 8/00* (2006.01)
*F16M 11/42* (2006.01)
*F16M 11/04* (2006.01)
*A47B 21/02* (2006.01)
*A47B 21/03* (2006.01)

(52) U.S. Cl.
CPC .......... *A61B 8/4405* (2013.01); *A61B 8/4427* (2013.01); *F16M 11/046* (2013.01); *F16M 11/048* (2013.01); *F16M 11/42* (2013.01); *A47B 2021/0364* (2013.01); *F16M 2200/028* (2013.01); *F16M 2200/041* (2013.01); *F16M 2200/063* (2013.01)

LOCK DEVICES AND SUPPORT ARMS THEREOF AND ULTRASOUND IMAGING SYSTEMS USING THE SAME

CROSS-REFERENCE TO RELATED APPLICATIONS

This application claims the benefit of Chinese Patent Application No. 201210294550.X, filed on Aug. 17, 2012, which is incorporated herein by reference.

TECHNICAL FIELD

The disclosure relates to medical ultrasound imaging systems and in particular to lock devices and support arms thereof and ultrasound imaging systems using the same.

BACKGROUND

When an ultrasound imaging system with lifting functions is operated by medical personnel, the control panel and/or display of the ultrasound imaging system may need to be able to rise and lower, at least within a certain range, usually based on requirements of operation, diagnosis or therapy. It would be beneficial for the control panel and/or display to be operated comfortably and locked at desired positions.

Control panels of cart-type ultrasound imaging systems currently existing in the market usually are able to rise and lower within a certain range, typically using a vertical lift or inclined lift mode. Vertical lift is particularly common. Regardless of whether vertical lift or inclined lift is used, the lifting system usually uses a gas spring with self-locking components to control the lifting. That is, the opening and closing of the valve of the gas spring are controlled by pulling a gas spring control rope via a handle on the control panel, thereby controlling the lifting and locking of the control panel. When the handle is pulled, the valve of the gas spring is opened and thus the control panel becomes liftable. When the handle is released, the valve of the gas spring is closed and the control panel is locked and cannot move.

There are other lifting systems, the control of the lifting of which are realized by electricity. That is, the lift and lock of the control panels are realized by controlling the extension and retraction of a screw rod via a stepping motor. By pressing a control button, the stepping motor is supplied with power and begins to work, which lifts the control panel. By releasing the control button, the stepping motor stops and the control panel is locked in place.

For the lifting structure to be supported and controlled by a gas spring with self-locking components, the requirement in forces required for balancing the control panel may be met within a period. However, for most gas springs, there are risks of gas leakage and force degradation, which lead to the support structure not being able to entirely support the control panel after a period of time and the operating force required will increase. Sometimes the force may be degraded too much to balance the gravity of the control panel, such that the self-lock force provided is substantially declined, leading to the self-lock no longer being able to be operated. In this case, the gas spring needs to be replaced, which will substantially increase the cost of maintenance and after-sales service. For a lifting system controlled by electricity, the screw rod can provide a larger self-lock force and it is not easy to fail. However, such lifting structure includes a controlling motor and can only be operated with a power supply, and the motor will generate noise when it is running, which will affect doctors and/or patients, and add to the cost.

SUMMARY

One of the aspects of the present disclosure is providing a lock device and a support arm thereof and an ultrasound imaging system using the same, where the lock device is simple and low cost.

Another one of the aspects of the present disclosure is providing a lock device and a support arm thereof and an ultrasound imaging system using the same, where the lock device is reliable and is able to bear a very large load.

Another one of the aspects of the present disclosure is providing a lock device and a support arm thereof and an ultrasound imaging system using the same, where the lock device will not generate noise, does not require electricity, and is easy to operate.

In some embodiments of the present disclosure, a lock device is provided. The lock device may comprise: a holder, which may be provided with a through hole running through the holder, where the holder may be further provided with a slide, and the slide may intersect with the through hole; a guide bar, which may be provided with an outer threaded area, where the guide bar may pass through the through hole and the outer threaded area may be located where the through hole intersects with the slide; a lock assembly comprising a lock component, where the lock component may be received in the slide and is able to move in the slide, one end of the lock component facing toward the guide bar may be provided with a lock threaded area, and the lock threaded area is able to engage with the outer threaded area; and a drive assembly which may drive the lock component to move toward or away from the guide bar in the slide to lock or unlock the lock device.

In some embodiments, the drive assembly may comprise: a drive slider, which may be connected to the holder and is able to move on the holder with respect to the holder, where one surface of the drive slider may contact with the lock component; and a drive device, one end of which may be connected to the drive slider; where on the surface of the drive slider contacting with the lock component, along a direction of movement of the drive slider on the holder, a thickness of at least one portion of the drive slider may be smaller than a thickness of at least another portion of the drive slider, and a transition surface may be provided between the at least one portion with smaller thickness and the at least another portion with larger thickness.

In some embodiments, the drive assembly may comprise: a carriage comprising a bottom wall and at least one sidewall extending from the bottom wall in a direction angled with respect to the bottom wall, where a receiving space may be formed between the bottom wall and the holder; a drive slider slidably received in the receiving space, where one surface of the drive slider may rest on the bottom wall and another surface of the drive slider may contact with the lock component, and the drive slider is able to move on the bottom wall; and a drive device, one end of which may be connected to the drive slider; where on the another surface of the drive slider contacting with the lock component, along a direction of movement of the drive slider on the bottom wall, a thickness of at least one portion of the drive slider may be smaller than a thickness of at least another portion of the drive slider, and a transition surface may be provided between the at least one portion with smaller thickness and the at least another portion with larger thickness.

In some embodiments, the drive assembly may further comprise a slider return spring. One end of the slider return spring may be connected to the at least one sidewall and the other end of the slider return spring may be connected to the drive slider.

In some embodiments, the drive assembly may further comprise a lock component return spring. One end of the lock component return spring may be connected to the lock component and the other end of the lock component return spring may be connected to the holder.

In some embodiments, the drive assembly may comprise: a lock component drive block which may be received in the slide and is able to move in the slide in an extension direction of the slide with respect to the holder, where at least a portion of the lock component drive block is able to contact with the lock component and a passage may be formed between the lock component drive block and the lock component, and the guide bar may pass through the passage; a drive slider which may be connected to the holder and is able to move on the holder with respect to the holder, where one surface of the drive slider may contact with the lock component drive block; and a drive device, one end of which may be connected to the drive slider; where on the surface of the drive slider contacting with the lock component drive block, along a direction of movement of the drive slider on the holder, a thickness of at least one portion of the drive slider may be smaller than a thickness of at least another portion of the drive slider, and a transition surface may be provided between the at least one portion with smaller thickness and the at least another portion with larger thickness.

In some embodiments, the drive assembly may comprise: a lock component drive block which may be received in the slide and is able to move in the slide in an extension direction of the slide with respect to the holder, where at least a portion of the lock component drive block is able to contact with the lock component and a passage may be formed between the lock component drive block and the lock component, and the guide bar may pass through the passage; a carriage comprising a bottom wall and at least one sidewall extending from the bottom wall in a direction angled with respect to the bottom wall, where the carriage may be connected to the holder and may be located above the slide, and a receiving space may be formed between the bottom wall and the holder; a drive slider slidably received in the receiving space, one surface of the drive slider may rest on the bottom wall and another surface of the drive slider may contact with the lock component drive block, and the drive slider is able to move on the bottom wall; and a drive device, one end of which may be connected to the drive slider; where on the another surface of the drive slider contacting with the lock component drive block, along a direction of movement of the drive slider on the bottom wall, a thickness of at least one portion of the drive slider may be smaller than a thickness of at least another portion of the drive slider, and a transition surface may be provided between the at least one portion with smaller thickness and the at least another portion with larger thickness.

In some embodiments, the drive assembly may further comprise a slider return spring. One end of the slider return spring may be connected to the at least one sidewall and the other end of the slider return spring may be connected to the drive slider.

In some embodiments, the drive assembly may comprise: a base which is connected to the holder; and a drive rod which may be slidably and rotatably connected to the lock component. One end of the drive rod may be rotatably connected to the base.

In some embodiments, the drive assembly may comprise: a lock component drive block which may be received in the slide and is able to move in the slide in an extension direction of the slide with respect to the holder, where at least a portion of the lock component drive block is able to contact with the lock component and a passage may be formed between the lock component drive block and the lock component, and the guide bar may pass through the passage; a base which may be connected to the holder; and a drive rod which may be slidably and rotatably connected to the lock component drive block. One end of the drive rod may be rotatably connected to the base.

In some embodiments, the drive assembly may further comprise a pin and the drive rod may be provided with a slot. The pin may pass through the slot and may be connected to the lock component. The drive rod is able to slide and rotate with respect to the pin.

In some embodiments, the drive assembly may further comprise a pin and the drive rod may be provided with a slot. The pin may pass through the slot and may be connected to the lock component drive block. The drive rod is able to slide and rotate with respect to the pin.

In some embodiments, the drive assembly may comprise: a base; a drive rod rotatably connected to the base, where one end of the drive rod may be rotatably connected to the lock component; and a restoring spring, where one end of the restoring spring may be connected to the drive rod and the other end of the restoring spring may be connected to the holder.

In some embodiments, the drive assembly may comprise: a lock component drive block, which may be received in the slide and is able to move in the slide in an extension direction of the slide with respect to the holder, where at least a portion of the lock component drive block is able to contact with the lock component and a passage may be formed between the lock component drive block and the lock component, and the guide bar may pass through the passage; a base; a drive rod rotatably connected to the base, where one end of the drive rod may be rotatably connected to the lock component drive block; and a restoring spring, where one end of the restoring spring may be connected to the drive rod and the other end of the restoring spring may be connected to the holder.

In some embodiments, one end of the slide facing toward the drive assembly may be open and the other end of the slide may be closed to form a bottom of the slide. The lock assembly may further comprise a return spring received in the slide. One end of the return spring may abut against the bottom of the slide and the other end of the return spring may abut against the lock component.

In some embodiments, the slide may run through the holder, and the lock assembly may further comprise: a return spring and a return spring press plate connected to the holder. One end of the return spring may abut against the return spring press plate and the other end of the return spring may abut against the lock component.

In some embodiments, the lock device may further comprise a support seat, one end of which may be connected to the holder.

In some embodiments, a support arm is provided. The support arm may comprise a first connection seat, a second connection seat, a first connection rod, and a second connection rod. One end of the first connection rod may be rotatably connected to the first connection seat and the other end of the first connection rod may be rotatably connected to the second connection seat, and one end of the second connection rod may be rotatably connected to the first connection seat and the other end of the second connection rod may be rotatably connected to the second connection seat. The support arm may further comprise a lock device as described above. One end of the lock device may be rotatably connected to the first connection seat and the other end of the lock device may be rotatably connected to the first connection rod.

In some embodiments, an ultrasound imaging system is provided. The ultrasound imaging system may comprise a support arm as described above.

DETAILED DESCRIPTION

Embodiments of the present disclosure now will be described in detail with reference to the drawings. Throughout the drawings and following description, like reference numbers refer to like or similar structures or components.

Figure 1:
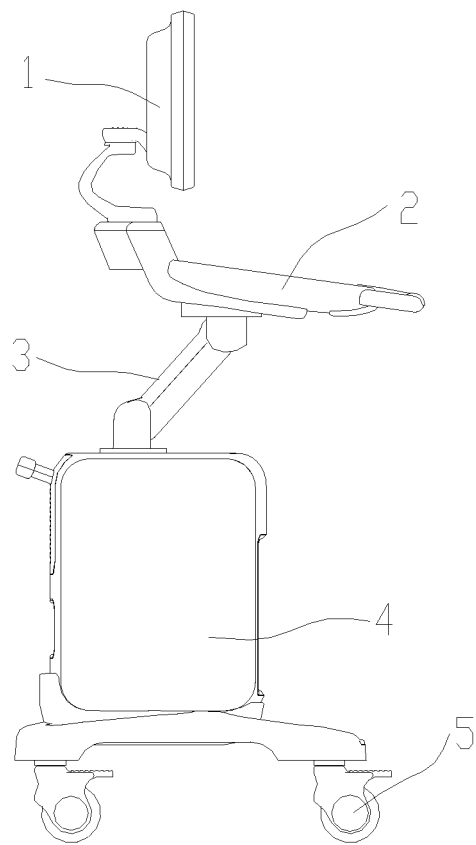
FIG. 1 is a schematic view of an ultrasound imaging system according to an embodiment of the present disclosure.

With reference to FIG. 1, according to an embodiment of the present disclosure, an ultrasound imaging system may include a display 1, a control panel 2, a support arm 3, a host 4 and caster wheels 5. The caster wheels 5 may be attached on a bottom portion of the host 4, by which the host 4 (therefore the whole ultrasound imaging system) can move on the ground. The support arm 3 may be attached to the host 4 at one end and to the control panel 2 at the other end, thereby making the control panel 2 to be connected to and rest on the host 4. The support arm 3 may rotate in a vertical direction, for example, rotating in a vertical plane clockwise or counterclockwise, thereby causing the control panel 2 to lower or rise (which will be described in detail in the following). The display 1 may be connected to the control panel 2.

According to this embodiment, the connections between the display 1 and the control panel 2, between the support arm 3 and the control panel 2 and the host 4 and between the caster wheels 5 and the host 4 may be common connections in the art and will not be described in detail.

Figure 2:
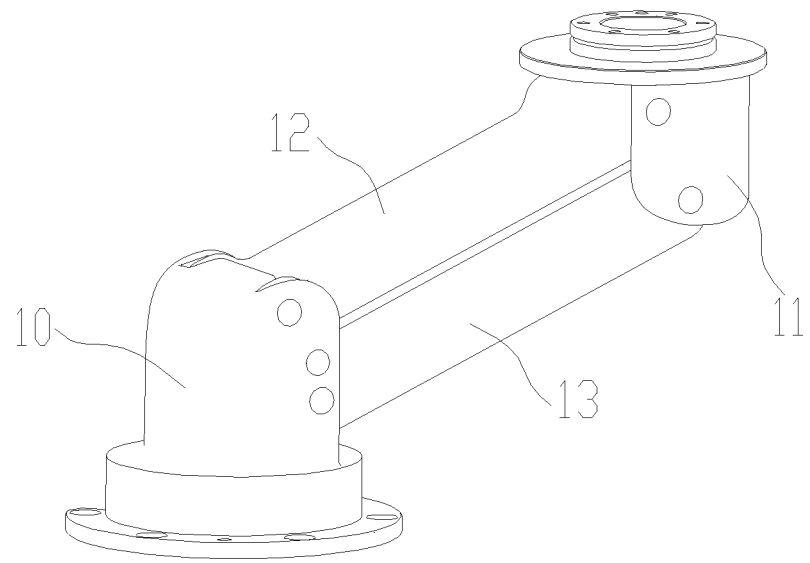
FIG. 2 is a schematic view of a support arm according to an embodiment of the present disclosure.
Figure 3:
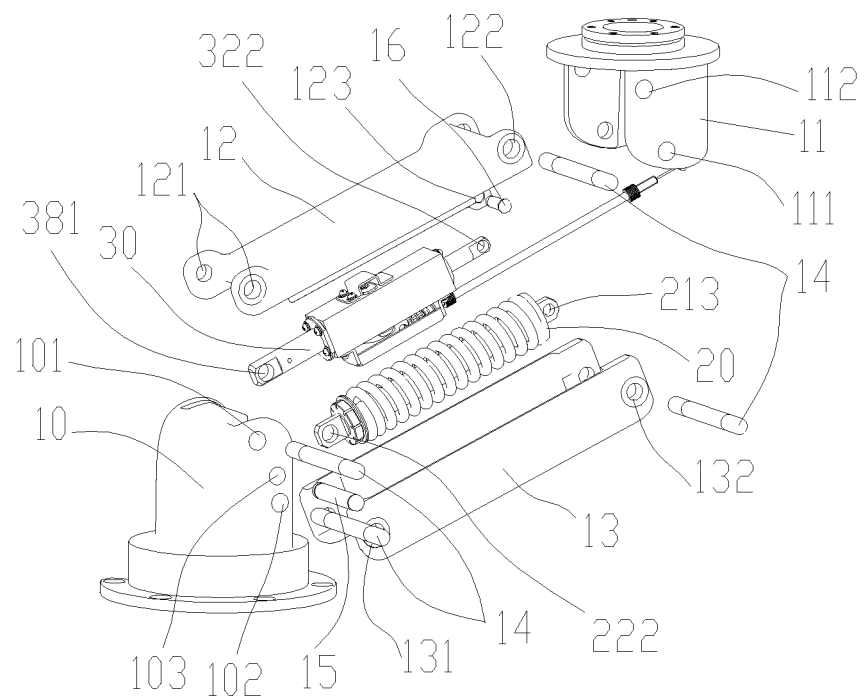
FIG. 3 is an exploded perspective view of a support arm according to an embodiment of the present disclosure.

With reference to FIG. 2 and FIG. 3, according to an embodiment of present disclosure, the support arm 3 may include a first connection seat 10, a second connection seat 11, a first connection rod 12 and a second connection rod 13. The first connection rod 12 may be rotatably connected to the first connection seat 10 at one end, and rotatably connected to the second connection seat 11 at the other end; the second connection rod 13 may be rotatably connected to the first connection seat 10 at one end, and rotatably connected to the second connection seat 11 at the other end. The first connection rod 12 may be parallel to the second connection rod 13 and may be located above the second connection rod 13 in a vertical direction. The first connection seat 10 may be connected to the host 4, and the second connection seat 11 may be connected to the control panel 2. The connection between the first connection seat 10 and the host 4 and between the second connection seat 11 and the control panel 2 may be a common connection in the art, such as a screw connection, a bolt connection, a threaded connection, a rivet connection, a weld, a snap connection, an interference fit connection, etc.

Thus, the first connection seat 10, the second connection seat 11, the first connection rod 12 and the second connection rod 13 may form a parallel four-link, which can rotate in a vertical plane clockwise or counterclockwise. Thus the control panel 2 connected to the second connection seat 11 may lower or rise.

With reference to FIG. 3, the first connection rod 12 may be provided with first mounting holes 121 at one end, and second mounting holes 122 at the other end. Correspondingly, the first connection seat 10 may be provided with third mounting holes 101, and the second connection seat 11 may be provided with fourth mounting holes 112. One of first connection shafts 14 may pass through the first mounting holes 121 and the third mounting holes 101, thereby rotatably connecting one end of the first connection rod 12 to the first connection seat 10. Another one of the first connection shafts 14 may pass through the second mounting holes 122 and the fourth mounting holes 112, thereby rotatably connecting the other end of the first connection rod 12 to the second connection seat 11.

Similarly, the second connection rod 13 may be provided with fifth mounting holes 131 at one end, and sixth mounting holes 132 at the other end. Correspondingly, the first connection seat 10 may be provided with seventh mounting holes 102, and the second connection seat 11 may be provided with eighth mounting holes 111. The seventh mounting holes 102 may be under the third mounting holes 101 in a vertical direction, and the eighth mounting holes 111 may be under the fourth mounting holes 112 in a vertical direction. One of the first connection shafts 14 may pass through the fifth mounting holes 131 and the seventh mounting holes 102, thereby rotatably connecting one end of the second connection rod 13 to the first connection seat 10. Another one of the first connection shafts 14 may pass through the sixth mounting holes 132 and the eighth mounting holes 111, thereby rotatably connecting the other end of the second connection rod 13 to the second connection seat 11.

Figure 4:
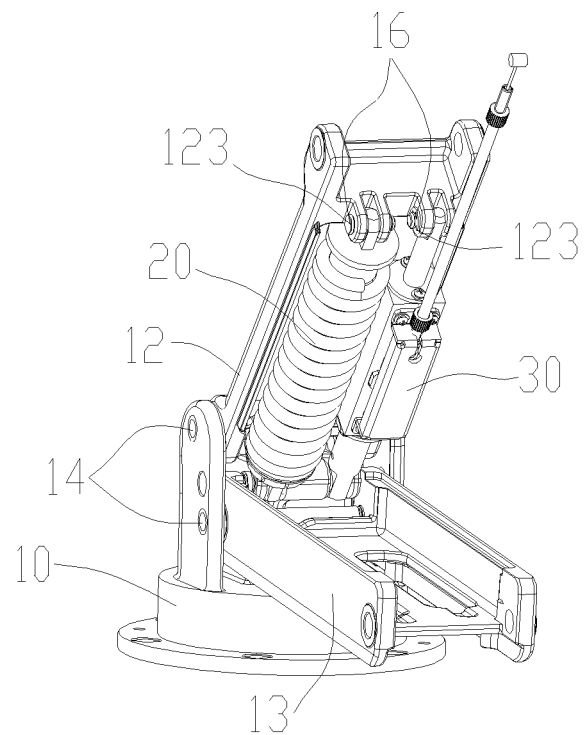
FIG. 4 is a schematic view of some components of a support arm according to an embodiment of the present disclosure.

With reference to FIG. 3 and FIG. 4, the support arm 3 may further include a damper 20 and a lock device 30. The damper 20 may be rotatably connected to the first connection seat 10 at one end, and rotatably connected to the first connection rod 12 at the other end. The lock device 30 may be rotatably connected to the first connection seat 10 at one end, and rotatably connected to the first connection rod 12 at the other end. The damper 20 and the lock device 30 may be located between the first connection rod 12 and the second connection rod 13 in a vertical direction.

The damper 20 may be provided with a first connection hole 222 at one end, and a second connection hole 213 at the other end. The lock device 30 may be provided with a third connection hole 381 at one end, and a fourth connection hole 322 at the other end. Correspondingly, the first connection seat 10 may be provided with a fifth connection hole 103 which may be located between the third mounting hole 101 and the seventh mounting hole 102 in a vertical direction. A second connection shaft 15 may pass through the first connection hole 222 of the damper 20, the third connection hole 381 of the lock device 30 and the fifth connection hole 103 of the first connection seat 10, thereby rotatably connecting one end of the damper 20 and one end of the lock device 30 to the first connection seat 10.

Similarly, the first connection rod 12 may be provided with a sixth connection hole 123, which may be located on the first connection rod 12 near the second mounting hole 122. A third connection shaft 16 may pass through the second connection hole 213 of the damper 20, the fourth connection hole 322 of the lock device 30 and the sixth connection hole 123 of the first connection rod 12, thereby rotatably connecting the other end of the damper 20 and the other end of the lock device 30 to the first connection rod 12.

In some embodiments of present disclosure, the connection between the damper 20 and the first connection seat 10 and the first connection rod 12 (for example, the fitting structure between the connection hole and the connection shaft) may be separated from or common with the connection between the lock device 30 and the first connection seat 10 and the first connection rod 12 (for example, the fitting structure between the connection hole and the connection shaft). For example, in the embodiment shown in FIG. 4, the connection between the damper 20 and the first connection rod 12 is separated from the connection between the lock device 30 and the first connection rod 12.

In some embodiments of the present disclosure, the damper 20 may be a damper known in the art. For example, the damper 20 may have the same structure as the balance arm 1 described in Chinese application 200910107866.1 filed on Jun. 19, 2009 by Shenzhen Mindray Bio-Medical Electronics CO., LTD and titled as "a support device for display," which is hereby incorporated herein by reference, or using other commerically-available balance arms or similar stuctures as known to a person of ordinary skill in the art.

Figure 5:
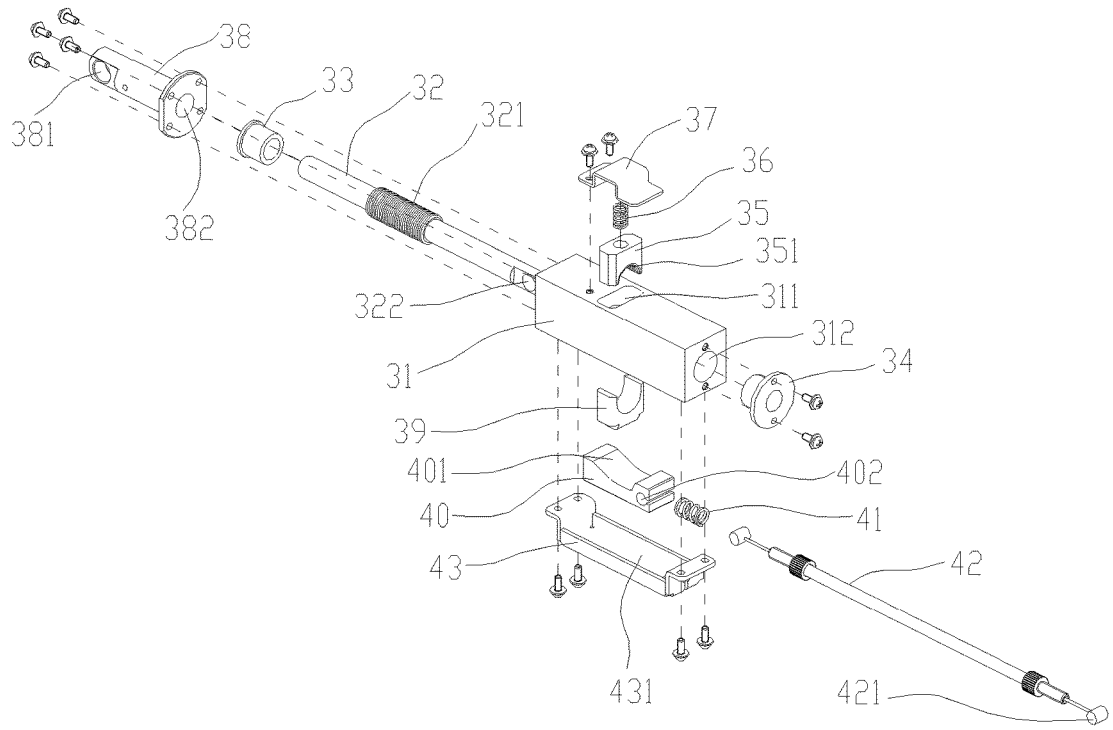
FIG. 5 is an exploded perspective view of a lock device according to an embodiment of the present disclosure.
Figure 6:
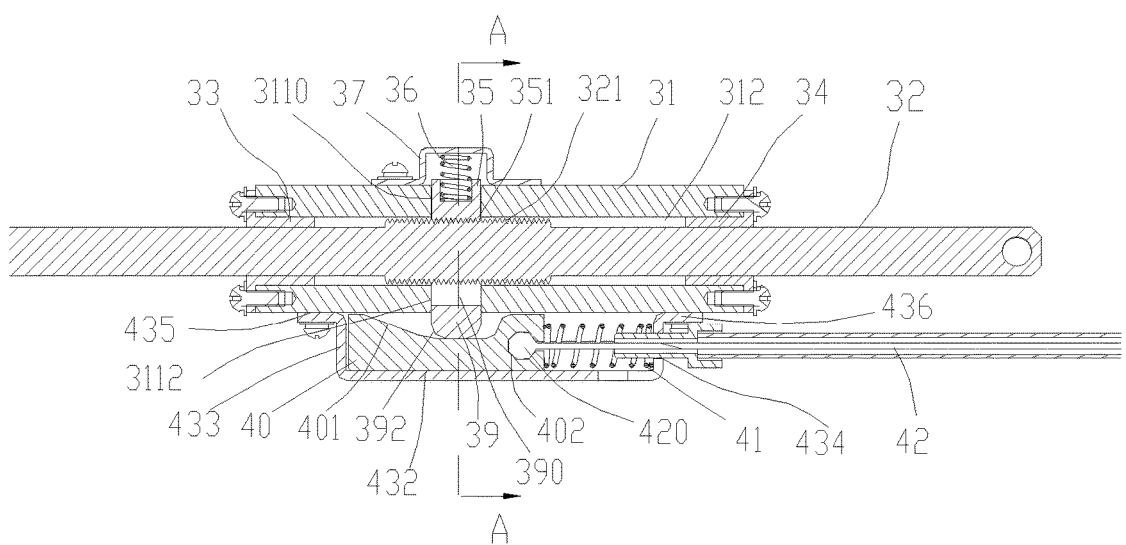
FIG. 6 is a schematic cross-sectional view of a lock device according to an embodiment of the present disclosure which is in locked state.
Figure 7:
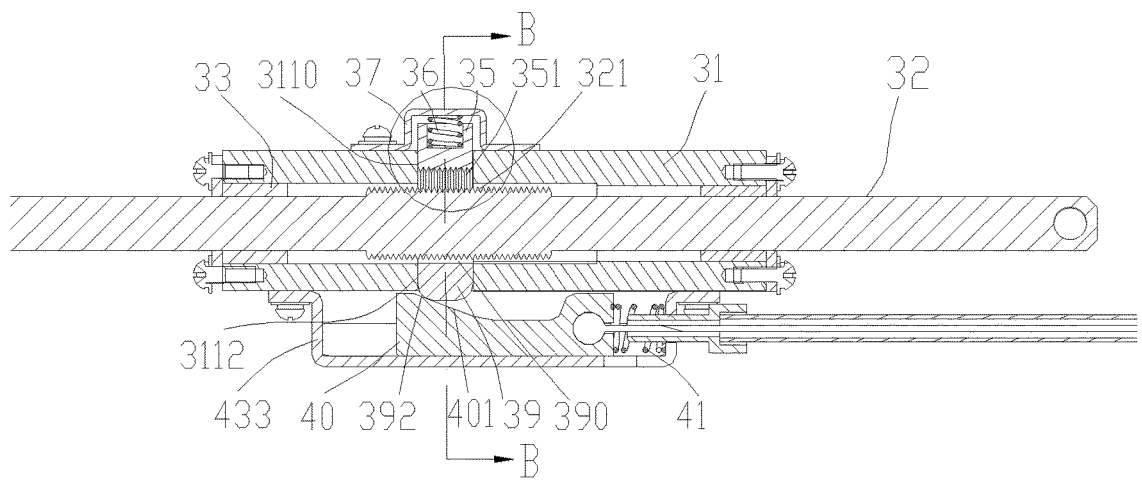
FIG. 7 is a schematic cross-sectional view of a lock device according to an embodiment of the present disclosure which is in unlocked state.

The lock device 30 according to some embodiments of the present disclosure will now be described in detail with reference to FIG. 5 to FIG. 7. FIG. 5 is an exploded perspective view of an embodiment of lock device 30, and FIG. 6 and FIG. 7 are longitudinal (length direction of the lock device 30) cross-sectional views of some components of an embodiment of lock device 30 which are in a locked state and an unlocked state, respectively.

As shown in FIG. 5, in an embodiment of the present disclosure, the lock device 30 may include a holder 31, a guide bar 32, a lock assembly and a drive assembly.

The holder 31 may be a lump-like structure. For example, the holder 31 may be a lump with any suitable shape, such as cuboid, cube, cylinder, prism, etc. For example, in the embodiments shown in FIG. 5 to FIG. 7, the holder 31 is a lump-like structure with a shape of cuboid. However, in embodiments of the present disclosure, the holder 31 may have any suitable shape.

The holder 31 may be provided with a through hole 312 which may run through the holder 31. The through hole 312 may extend from one end face to the other end face of the holder 31, thereby running through the holder 31. The holder 31 may further be provided with a slide 311 which may extend in a direction intersecting with the extension direction of the through hole 312 and communicate with the through hole 312. In some embodiments of the present disclosure, the extension direction of the slide 311 may be perpendicular to or angled with the extension direction of the through hole 312.

In some embodiments of the present disclosure (for example, the embodiments shown in FIG. 5 to FIG. 7), the slide 311 may also run through the holder 31. That is, the slide 311 may extend from one end face to the other end face of the holder 31, thereby running through the holder 31. Furthermore, the slide 311 may intersect with the through hole 312 and communicate with it. That is, as shown in FIG. 6 to FIG. 7, with respect to the through hole 312, the slide 311 may include a first slide 3110 located at one side of the through hole 312 and a second slide 3112 located at the other side of the through hole 312.

The guide bar 32 may be provided with the fourth connection hole 322 (i.e., the fourth connection hole 322 of the lock device 30 mentioned above) at one end. At least one portion of the outer surface of the guide bar 32 may be provided with outer threads to form an outer threaded area 321.

As shown in FIG. 6 and FIG. 7, the guide bar 32 may pass through the through hole 312 of the holder 31 and the outer threaded area 321 may be located where the through hole 312 intersects with the slide 311 (for example, the first slide 3110 and the second slide 3112).

In some embodiments of the present disclosure, the lock device 30 may further include a first sleeve 33 and a second sleeve 34 which may be located at two ends of the through hole 312 respectively and connected to the holder 31. The first sleeve 33 and the second sleeve 34 may be connected to the holder 31 by way of a common mechanical connection, such as a screw connection, a threaded connection, a snap connection, a press fit connection, an interference fit connection, etc. For example, in the embodiment shown in FIG. 5, the first sleeve 33 may be pressed onto the holder 31 by a support seat 38 (described in detail hereinafter) or connected to the holder 31 by an interference fit with the internal surface of the through hole 312, while the second sleeve 34 may be connected to the holder 31 by a screw. In the embodiments shown in FIG. 6 and FIG. 7, both of the first sleeve 33 and the second sleeve 34 may be connected to the holder 31 by screws.

The first sleeve 33 may be provided with a shaft hole, which may run through the first sleeve 33, and the second sleeve 34 may be provided with a shaft hole which may run through the second sleeve 34. The guide bar 32 may pass through the shaft hole of the first sleeve 33 and the shaft hole of the second sleeve 34, as shown in FIG. 6 and FIG. 7. When the lock device 30 is in an unlocked state (as described in detail hereinafter), the guide bar 32 is able to move in a longitudinal direction in the through hole 312, the shaft hole of the first sleeve 33 and the shaft hole of the second sleeve 34 with respect to the holder 31, the first sleeve 33 and the second sleeve 34. In the present disclosure, the "longitudinal direction" mentioned above may refer to the length direction of the lock device 30, for example, the axial direction of the guide bar 32, and also, for example, the extension direction in which the through hole 312 extends from one end face to the other end face of the holder 31.

In some embodiments of the present disclosure, the lock device 30 may further include a support seat 38. The support seat 38 may be provided with the third connection hole 381 (i.e., the third connection hole 381 of the lock device 30 mentioned above) at one end, and a receive hole 382 at the other end. The end of the support seat 38 at which the receive hole 382 is provided with may be connected to the holder 31. For example, in the embodiment shown in FIG. 5, the end of the support seat 38 at which the receive hole 382 is provided with may be provided with a flange on which screw holes may be provided. Screws may pass through the screw holes to connect the support seat 38 to the holder 31. However, it will be appreciated that, in some embodiments of the present disclosure, the end of the support seat 38 at which the receive hole 382 is provided with may also be connected to the holder 31 by other suitable ways.

One end of the guide bar 32 opposite to the end at which the fourth connection hole 322 is provided with may be received in the receive hole 382 of the support seat 38 and is able to move in the receive hole 382 with respect to the support seat 38.

In some embodiments of the present disclosure, when the through hole 312 of the holder 31 has enough length to provide enough space for the movement of the guide bar 32, the receive hole 382 provided at one end of the support seat 38 may not be necessary. In this case, one end of the support seat 38 may be connected to the holder 31 and the other end may be provided with the third connection hole 381 (i.e., the third connection hole 381 of the lock device 30 mentioned above). The support seat 38 may be rotatably connected to the first connection seat 10 via the third connection hole 381.

In some embodiments of the present disclosure, the support seat 38 may be integrated with the holder 31, but not a separated component from the holder 31. That is, the support seat 38 may be directly formed on the holder 31.

Thus, as mentioned above, one end of the lock device 30 may be rotatably connected to the first connection seat 10 via the third connection hole 381, and the other end of the lock device 30 may be rotatably connected to the first connection rod 12 via the fourth connection hole 322, thereby installing the lock device 30 in the support arm 3 entirely.

With reference to FIG. 5 through FIG. 10, in an embodiment of the present disclosure, the lock assembly of the lock device 30 may include a lock component 35, a return spring 36 and a return spring press plate 37. The lock component 35 may be received in the slide 311 and is able to slide in the slide 311 in the extension direction of the slide 311. In some embodiments, as shown in FIG. 6 and FIG. 7, the lock component 35 may be received in the first slide 3110 of the slide 311 and is able to slide in the first slide 3110 in the extension direction of the slide 311 (for example, of the first slide 3110). The return spring press plate 37 may be connected to the surface of the holder 31 and be located above the slide 311. The return spring press plate 37 may be connected to the surface of the holder 31 by common connection, such as a screw connection, a weld, a rivet connection, etc. The return spring 36 mat be located between the return spring press plate 37 and the lock component 35. That is, one end of the return spring 36 may abut against the return spring press plate 37 and the other end against the lock component 35.

The lock component 35 may be received in the first slide 3110. As mentioned above, the first slide 3110 may be located at one side of the through hole 312 and communicate with the through hole 312, the guide bar 32 may pass through the through hole 312, and the outer threaded area 321 of the guide bar 32 may be located where the through hole 312 intersects with the first slide 3110. Therefore, the end of the lock component 35 received in the first slide 3110 may face toward the guide bar 32 (for example, face toward the outer threaded area 321 of the guide bar 32), while the other end of the lock component 35 may face toward the return spring 36 and the return spring press plate 37, and one end of the return spring 36 may abut against such other end of the lock component 35.

Figure 8:
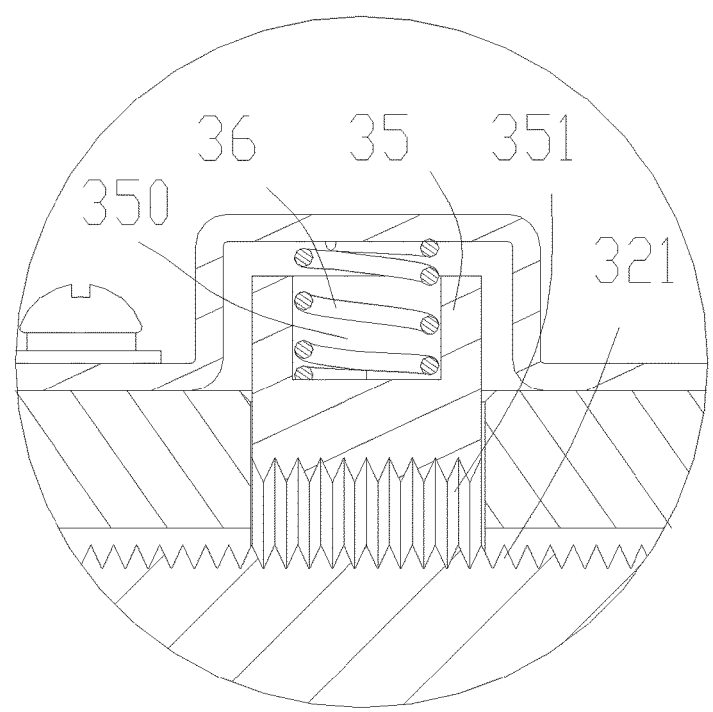
FIG. 8 is an enlarged schematic view of the components within the circle in FIG. 7.

With reference to FIG. 8, in some embodiments of the present disclosure, the end of the lock component 35 facing toward the return spring 36 may be provided with a spring receive hole 350 in which at least a portion of the return spring 36 may be received. This way, one end of the return spring 36 may abut against the bottom of the spring receive hole 350 and the other end against the return spring press plate 37.

In some embodiments of the present disclosure, the slide 311 may not run through the surface of the holder 31 which is far away from the drive assembly, and such surface may be closed, for example, the slide 311 (or the first slide 3110) may be a one-end-opened slide. That is, the end of the slide 311 facing toward the drive assembly (or facing toward the guide bar 32) may be opened, while the other end may be closed. The slide may have a closed bottom. The return spring 36 may be received in the slide 311 (or the first slide 3110) and one end of the return spring 36 may abut against the bottom of the slide 311 (or the first slide 3110) while the other end is against the lock component 35. In this case, in some embodiments, the return spring press plate 37 may be not necessary.

In some embodiments of the present disclosure, the end of the lock component 35 facing toward the guide bar 32 may be provided with a lock threaded area 351 on which threads may engage with the outer threads on the outer threaded area 321 of the guide bar 32. This way, the lock threaded area 351 may engage with the outer threaded area 321 of the guide bar 32.

In some embodiments of the present disclosure, the contour shape of the lock threaded area 351 of the lock component 35 may correspond to the contour shape of the outer threaded area 321 of the guide bar 32 so as to facilitate the engagement of the lock threaded area 351 with the outer threaded area 321. For example, the contour shape of the lock threaded area 351 may be arc-shaped shape, semicircle, etc.

In some embodiments of the present disclosure, the return spring 36 may be any spring which is suitable for providing restoring force for the lock component 35. For example, in some embodiments, the return spring 36 may be a compression spring, a disc spring, etc.

With reference to FIG. 5 to FIG. 10, in some embodiments of the present disclosure, the drive assembly of the lock device 30 may include a lock component drive block 39, a drive slider 40, a slider return spring 41, a drive device 42 and a carriage 43.

The lock component drive block 39 may be received in the slide 311 and may be opposite to the lock component 35 received in the slide 311, and may move in the slide 311 in the extension direction of the slide 311 with respect to the holder 31. At least a portion of the lock component drive block 39 may contact with the lock component 35 and push the lock component 35 to bring it to move in the slide 311. A passage 390 may be formed between the lock component drive block 39 and the lock component 35. The passage 390 may enable the guide bar 32 to pass through it and enable the lock component drive block 39 and the lock component 35 to move in the slide 311 in a range. That is, the passage 390 may run through the lock component drive block 39 and the lock component 35 in the longitudinal direction of the guide bar 32, the guide bar 32 may pass through the passage 390 between the lock component drive block 39 and the lock component 35, and the width of the passage 390 formed between the lock component drive block 39 and the lock component 35 in the direction of the movement of the lock component drive block 39 and the lock component 35 (for example, the extension direction of the slide 311) is wider than the diameter of the outer threaded area 321 of the guide bar 32.

Figure 9:
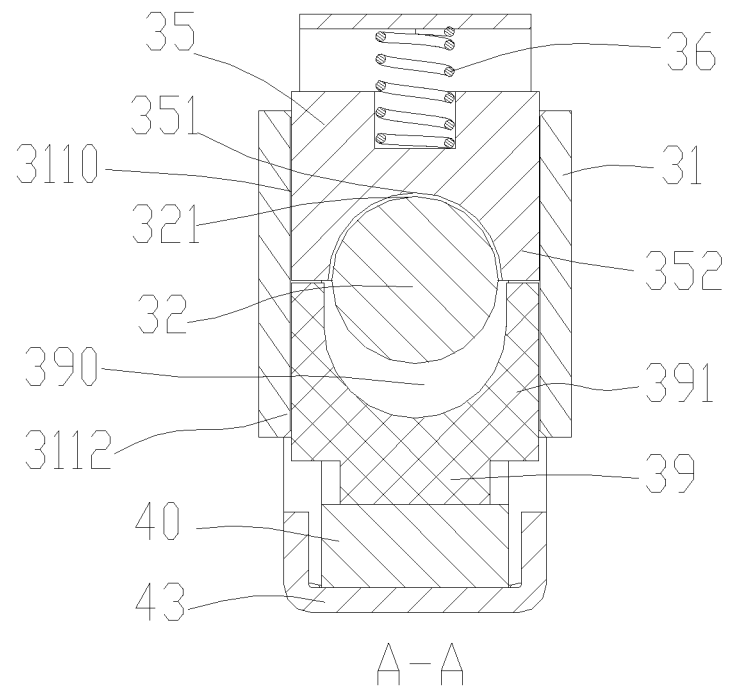
FIG. 9 is a schematic cross-sectional view taken along line A-A in FIG. 6.
Figure 10:
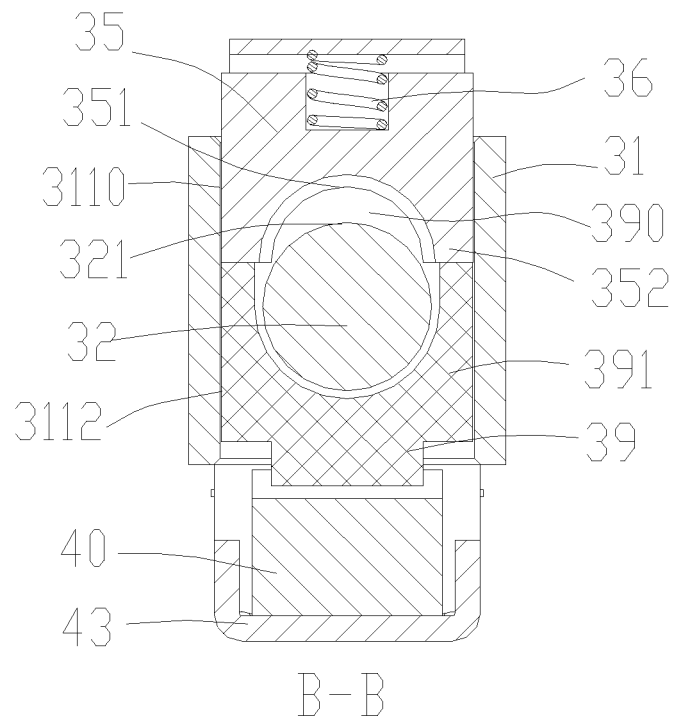
FIG. 10 is a schematic cross-sectional view taken along line B-B in FIG. 7.

For example, as shown in FIG. 9 and FIG. 10, in some embodiments of the present disclosure, the lock component drive block 39 may be received in the second slide 3112 and may move in the second slide 3112 in the extension direction of the second slide 3112. The end of the lock component drive block 39 facing toward the lock component 35 may be provided with a U-shaped groove with a "U-shaped" cross-sectional shape. Correspondingly, a cross-section of the lock threaded area 351 provided on the end of the lock component 35 facing toward the guide bar 32 (for example, facing toward the lock component drive block 39) may be a semicircle. The groove may be opposite to the lock threaded area 351 and at least one of the sidewalls 391 of the groove of the lock component drive block 39 may contact with at least one of the lock threaded sidewalls 352 of the lock threaded area 351 of the lock component 35. Thus, the U-shaped groove and the lock threaded area 351 which are opposite to each other may form the passage 390 through which the guide bar 32 may pass.

In some embodiments, the lock threaded area 351 of the lock component 35 may be formed to run through the lock component 35 in the longitudinal direction of the guide bar 32. The threads provided on the lock threaded area 351 may be provided on either the entire or at least a portion of the lock threaded area 351 running through the lock component 35.

In some embodiments of the present disclosure, the passage 390 through which the guide bar 32 may pass and which may enable the lock component drive block 39 and the lock component 35 to move in the slide 311 in a range is not limited to being formed by the groove with a U-shaped cross-section and the lock threaded area 351 with a semicircular cross-section opposite to each other shown in the embodiments of FIG. 9 and FIG. 10, rather, the passage 390 may also be formed by a groove with any other suitable cross-sectional shape and a lock threaded area with any other suitable cross-sectional shape, for example, the shape of the cross-section of the groove may be an ellipse, an arc, a square, a rectangle, a polygon, a parabolic shape, an irregular curve or zigzag, etc.; the lock threaded area may be arc-shaped or of other shapes, as long as at least a portion of the threads on the lock threaded area can engage with at least a portion of the outer threads on the outer threaded area 321 of the guide bar 32; or, the surface of the end of the lock component drive block 39 facing toward the lock component 35 may be flat and not provided with a groove, rather, at least one drive rod or drive arm may be protruded from the surface, the at least one drive rod or drive arm may contact with the lock component 35 and push the lock component 35 to move in the slide 311, the passage 390 as mentioned above may be formed between the lock component 35 and the surface of the lock component drive block 39 facing toward the lock component 35 and the at least one drive rod or drive arm, etc., as long as the guide bar 32 is able to pass through between the lock component drive block 39 and the lock component 35 and the lock component drive block 39 and the lock component 35 are able to move in the slide 311 in a certain range.

With reference to FIG. 5 to FIG. 7, in some embodiments of the present disclosure, the carriage 43 may include a bottom wall 432 and a first sidewall 433 and/or a second sidewall 434 extending from the edge of the bottom wall 432 at a certain angle with respect to the bottom wall 432. The end of the first sidewall 433 away from the bottom wall 432 may be provided with a first connection portion 435, and the end of the second sidewall 434 away from the bottom wall 432 may be provided with a second connection portion 436. The carriage 43 may be connected to the side of the holder 31 on which the slide 311 (for example, the second slide 3112) may be located via the first connection portion 435 and the second connection portion 436, and the bottom wall 432 may be brought to be opposite to the second slide 3112. Thus, the bottom wall 432, the first sidewall 433, the second sidewall 434 and the surface of the holder 31 may define a receiving space 431. A drive slider 40 may be received in the receiving space 431 and rest on the bottom wall 432 of the carriage 43, and be able to slide on the bottom wall 432.

The drive slider 40 may be provided with a drive slider connection portion 402 at one end. Correspondingly, the drive device 42 may be provided with a drive device connection portion 420 at one end. The drive device connection portion 420 may be connected to the drive slider connection portion 402, thereby connecting one end of the drive device 42 to the drive slider 40. The connection between the drive slider connection portion 402 and the drive device connection portion 420 may be of a variety of types, for example, a snap connection where the drive slider connection portion 402 is a slot while the drive device connection portion 420 is a hook, a screw connection where the drive slider connection portion 402 is a threaded hole while the drive device connection portion 420 is a threaded stud, a connection where the drive slider connection portion 402 is a clasp while the drive device connection portion 420 is a ring, etc. For example, in the embodiments shown in FIG. 6 and FIG. 7, the drive slider connection portion 402 is a slot while the drive device connection portion 420 is a connection head which is engaged in the slot.

The drive device connection portion 420 at one end of the drive device 42 may be connected to the drive slider connection portion 402, and the other end of the drive device 42 (i.e., operation end 421) may extend through openings (not shown in the drawings) in the second sidewall 434 of the carriage 43. The slider return spring 41 may be sleeved on the drive device 42 and located between the drive slider 40 and the second sidewall 434 of the carriage 43. The slider return spring 41 may abut against the drive slider 40 at one end, and against the second sidewall 434 of the carriage 43 at the other end. Thus, the drive device 42 may be operated by operating the operation end 421, thereby driving the drive slider 40 to move on the bottom wall 432 of the carriage 43. When the force operating the operation end 421 is released, the drive slider 40 can return to the original position through the action of the slider return spring 41.

In some embodiments of the present disclosure, the slider return spring 41 may be any spring which is suitable for providing restoring force for the drive slider 40, for example, a compression spring, a disc spring, a tension spring or any other suitable elastic element, etc. For example, in the embodiments shown in FIG. 6 and FIG. 7, the slider return spring 41 may be a compression spring, a disc spring, etc.

In the embodiments shown in FIG. 6 and FIG. 7, it is also possible that only the second sidewall 434 is provided without the first sidewall 433.

One surface of the drive slider 40 may rest on the bottom wall 432 of the carriage 43, and another surface opposite to the surface resting on the bottom wall 432 may contact with the lock component drive block 39 received in the slide 311 (or the second slide 3112).

In some embodiments of the present disclosure, the surface of the drive slider 40 contacting with the lock component drive block 39 may be provided with a recess or protrusion which may extend in the direction of the movement of the drive slider 40 on the bottom wall 432. That is, on the surface of the drive slider 40 contacting with the lock component drive block 39, in the direction of the movement of the drive slider 40 on the bottom wall 432, the thickness of at least one portion of the drive slider 40 may be smaller than that of at least another portion of the drive slider 40, and a transition surface may be provided from the at least one portion with smaller thickness to the at least another portion with larger thickness. Here, said "thickness" of the drive slider 40 may mean the thickness of the drive slider 40 in a cross-section parallel to the plane defined by the direction of the movement of the lock component drive block 39 and the direction of the movement of the drive slider 40 (in the embodiments shown in FIG. 6 and FIG. 7, the cross-section represented by FIG. 6 and FIG. 7).

For example, in the embodiments shown in FIG. 6 and FIG. 7, the surface of the drive slider 40 contacting with the lock component drive block 39 may be provided with a recess. The drive slider 40 may have a small thickness at the recess, and have a larger thickness at the locations which are away from the slider return spring 41 and the recess in the direction of the movement of the drive slider 40 on the bottom wall 432 (i.e., the left and right direction in FIG. 6 and FIG. 7). The location with a smaller thickness may be smoothly transited to the location with a larger thickness via a slope. However, in some embodiments of the present disclosure, the transition surfaces from the location with a smaller thickness to the location with a larger thickness are not limited to the slope, but may be realized by any suitable curve.

Now the work process of some embodiments of present disclosure will be described with reference to FIG. 6 to FIG. 10.

First, with reference to FIG. 6 and FIG. 9, where FIG. 9 is a cross-sectional view of the embodiment of FIG. 6 taken along the line A-A. In FIG. 6 and FIG. 9, the lock device 30 is in a locked state. In this case, the lock component drive block 39 abuts against the location of the drive slider 40 with a smaller thickness (in the case of FIG. 6, i.e., abuts against the recess on the surface of the drive slider 40 facing toward the lock component drive block 39), while the lock component 35 abuts against the outer threaded area 321 of the guide bar 32 under the action of the return spring 36, and at least a portion of the threads on the lock threaded area 351 of the lock component engages with at least a portion of the outer threads on the outer threaded area 321 of the guide bar 32. This way, due to the engagement of at least a portion of threads on the lock threaded area 351 of the lock component 35 with at least a portion of the outer threads on the outer threaded area 321 of the guide bar 32, the guide bar 32 cannot move in the longitudinal direction of the guide bar 32 with respect to the lock component 35, therefore with respect to the holder 31, such that the lock device 30 wholly cannot be compressed or stretched in the longitudinal direction of the guide bar 32. Because in the longitudinal direction of the guide bar 32 the lock device 30 is connected to the first connection seat 10 of the support arm 3 at one end and to the first connection rod 12 of the support arm 3 at the other end, when the lock device 30 cannot be compressed or stretched in the longitudinal direction of the guide bar 32, the first connection rod 12 cannot rotate with respect to the first connection seat 10, such that the support arm 3 cannot rotate. Therefore, the support arm 3 may be locked.

With reference FIG. 7 and FIG. 10 now, where FIG. 10 is a cross-sectional view of the embodiment of FIG. 7 taken along the line B-B. In FIG. 7 and FIG. 10, the lock device 30 is in an unlocked state.

When the support arm 3 needs to be unlocked, the user may operate the drive device 42 via the operation end 421 of the drive device 42. The drive device 42 drives the drive slider 40 to move toward the second sidewall 434 of the carriage 43 on the bottom wall 432 of the carriage 43 with respect to the holder 31 and the lock component drive block 39 and compress the slider return spring 41. Due to the movement of the drive slider 40, the contact position of the lock component drive block 39 with the drive slider 40 is moved from a location with a smaller thickness (for example, as shown in FIG. 6) through the transition surface (for example, the slope 401) to a location with a larger thickness. During this movement, the drive slider 40 will push the lock component drive block 39 with which the drive slider 40 contacts to move away from the drive slider 40 in the slide 311 (for example, the second slide 3112) of the holder 31. The lock component drive block 39 in turn pushes the lock component 35 to move in a direction away from the guide bar 32 in the slide 311 (for example, the first slide 3110) and compress the return spring 36. Because the lock component 35 is pushed away from the guide bar 32, the threads on the lock threaded area 351 of the lock component 35 disengage from the outer threads on the outer threaded area 321 of the guide bar 32, as shown in FIG. 8. Therefore, the guide bar 32 can move in the longitudinal direction of the guide bar 32 with respect to the holder 31, such that the lock device 30 can be compressed or stretched in the longitudinal direction of the guide bar 32. Because in the longitudinal direction of the guide bar 32 the lock device 30 is connected to the first connection seat 10 of the support arm 3 at one end and to the first connection rod 12 of the support arm 3 at the other end, when the lock device 30 can be compressed or stretched in the longitudinal direction of the guide bar 32, the first connection rod 12 can rotate with respect to the first connection seat 10, such that the support arm 3 can rotate. Therefore, the support arm 3 may be unlocked.

When the support arm 3 reaches a desired position and needs to be locked again, the drive force on the drive device 42 may be released. At this time, under the action of the slider return spring 41, the drive slider 40 move away from the second sidewall 434 on the bottom wall 432 of the carriage 43 with respect to the holder 31 and the lock component drive block 39, while under the action of the return spring 36, the lock component 35 moves toward the guide bar 32 in the slide 311 (for example, the first slide 3110), and therefore pushes the lock component drive block 39 to move away from the guide bar 32 (i.e., toward the drive slider 40) in the slide 311 (for example, the second slide 3112) until at least a portion of the threads on the lock threaded area 351 of the lock component 35 engage with at least a portion of outer threads on the outer threaded area 321 of the guide bar 32. This way, the contact position of the lock component drive block 39 with the drive slider 40 is moved from the location with a larger thickness through the transition surface (for example, the slope 401) back to the location with a smaller thickness. Therefore, the guide bar 32 may be locked again, i.e., the lock device 30 and the support arm 3 may be locked again.

In some embodiments of the present disclosure, the surface of the lock component drive block 39 contacting with the drive slider 40 may further be provided with slide surface 392, which may be a smooth arc-shaped or curvilinear surface so as to facilitate the slide of the lock component drive block 39 on the drive slider 40.

In some embodiments shown in FIG. 6 and FIG. 7, the slider return spring 41 may be a compression spring or disc spring, and may be provided between the drive slider 40 and the second sidewall 434 of the carriage 43. The slider return spring 41 may provide restoring force for the drive slider 40 via the elastic force resulting from being compressed. However, in some embodiments of the present disclosure, the slider return spring 41 may also be provided at other locations and provide restoring force for the drive slider 40 in other ways. For example, in some embodiments of the present disclosure, the slider return spring 41 may also be provided between the first sidewall 433 of the carriage 43 and the drive slider 40 (not shown in the drawings). The slider return spring 41 may be connected to the first sidewall 433 at one end and to the drive slider 40 at the other end. The connections of the slider return spring 41 with the first sidewall 433 and the drive slider 40 may be any suitable connection, such as a snap connection, screw connection, bolt connection, etc.

In some embodiments, the slider return spring 41 may be a tension spring. When the drive device 42 drives the drive slider 40 to move toward the second sidewall 434 of the carriage 43, the slider return spring 41 is stretched, thereby providing restoring force for the drive slider 40 via the elastic force resulting from being stretched.

According to what is described above, it will be understood that in some embodiments of the present disclosure, it may be possible that only one of the first sidewall 433 and the second sidewall 434 is provided for connecting the slider return spring 41.

For example, in some embodiments, the carriage 43 may include a bottom wall 432 and at least one sidewall extending from the bottom wall 432 in a direction angled with respect to the bottom wall 432. The slider return spring 41 may be connected to or abut against the at least one sidewall to provide restoring force for the drive slider 40. The carriage 43 may be connected to the holder 31 and the bottom wall 432 of the carriage 43 may be located above the slide 311 of the holder 31. That is, the bottom wall 432 may be opposite to the slide 311, thereby forming the receiving space 431 between the bottom wall 432 and the holder 31. The drive slider 40 may be received in the receiving space 431.

In some embodiments of the present disclosure, the slider return spring 41 may be a compression spring, disc spring, tension spring or any other suitable elastic element. The slider return spring 41 may be connected to or abut against the at least one sidewall of the carriage 43 at one end, and connected to or abut against the drive slider 40 at the other end. In present disclosure, the slider return spring 41 being connected to or abutting against the at least one sidewall and the drive slider 40 is collectively referred to as the slider return spring 41 being "connected to" the at least one sidewall and the drive slider 40.

In the embodiments shown in FIG. 6 and FIG. 7, the carriage 43 may be connected to the holder 31 through the connection portions 435, 436 arranged on the first sidewall 433 and the second sidewall 434. However, in other embodiments of the present disclosure, the connection portions for connecting the holder 31 may not be provided on the first sidewall 433 and the second sidewall 434. Rather, at least one connection sidewall may be provided in the carriage 43. The at least one connection sidewall may extend from a suitable location on the bottom wall 432 in a direction angled with respect to the bottom wall 432. The connection portion connecting with the holder 31 may be provided on the at least one connection sidewall.

In some embodiments of the present disclosure, the drive device 42 may drive the drive slider 40 to move in the carriage 43. The drive device 42 may drive the drive slider 40 by pulling or pushing or any other suitable ways which are able to drive the drive slider 40 to move in the carriage 43.

For example, in the embodiments shown in FIG. 6 and FIG. 7, the drive device 42 may be a pull cable. In other embodiments of the present disclosure, the drive device 42 may be a pushrod, one end of which may pass through the second sidewall 434 of the carriage 43 and be connected to the drive slider 40. The slider return spring 41 may be a tension spring and may be provided between the drive slider 40 and the second sidewall 434, that is, one end of the slider return spring 41 may be connected to the drive slider 40 and the other end may be connected to the second sidewall 434. The connection of the slider return spring 41 with the second sidewall 433 and the drive slider 40 may be any suitable connection, such as a snap connection, thread connection, screw connection, etc. The locations where the drive slider 40 has a larger thickness as mentioned above may be near the second sidewall 434, the locations where the drive slider 40 has a smaller thickness may be away from the second sidewall 434, and the locations with a larger thickness and the locations with a smaller thickness may be connected with a transition surface. This way, by pushing the pushrod, the drive slider 40 may be pushed to move away from the second sidewall 434 on the bottom wall 432 of the carriage 43 and stretch the slider return spring 41, and the contact position of the lock component drive block 39 with the drive slider 40 may be moved from the locations with a smaller thickness to the locations with a larger thickness. Therefore, the lock component 35 may be pushed to unlock the support arm 3, as described in the embodiments above. When the push force pushing the pushrod is removed, under the action of the stretching force of the slider return spring 41, the drive slider 40 may be pulled to move toward the second sidewall 434, such that the contact position of the lock component drive block 39 with the drive slider 40 may be moved from the locations with a larger thickness back to the locations with a smaller thickness, while the return spring 36 may push the lock component 35 to move toward the guide bar 32 and lock the guide bar 32 as described in aforementioned embodiments.

In some embodiments, the slider return spring 41 also may be provided between the first sidewall 433 of the carriage 43 and the drive slider 40. When the drive slider 40 is pushed by the pushrod to move away from the second sidewall 434 (i.e., toward the first sidewall 433), the slider return spring 41 is compressed, thereby providing the restoring force for the drive slider 40 via the elastic force resulting from being compressed. In this case, the slider return spring 41 may be a compression spring or disc spring.

In such embodiments, other structures may be same as those in the embodiments aforementioned and will not be described in detail.

In the embodiments shown in FIG. 6 and FIG. 7, the lock component 35 may be received in the first slide 3110 of the slide 311, and the drive assembly of the lock device 30 may include lock component drive block 39 and the drive slider 40 and the lock component drive block 39 may be received in the second slide 3112 of the slide 311. The drive slider 40 may push the lock component 35 by driving the lock component drive block 39. However, in other embodiments of the present disclosure, the drive assembly of the lock device 30 also may not include the lock component drive block 39. Rather, the lock component 35 may be driven directly by the drive slider 40.

For example, in other embodiments of the present disclosure, the slide 311 in the holder 31 may further include the second slider 3112. The lock component 35 may be received in the second slider 3112, and the lock threaded area 351 on the lock component 35 may face toward the outer threaded area 321 of the guide bar 32. At least a portion of the threads on the lock threaded area 351 may engage with at least a portion of the threads on the outer threaded area 321. The end of the lock component 35 opposite to the lock threaded area 351 may contact with the surface of the drive slider 40. The surface of the drive slider 40 contacting with the lock component 35 may be provided with a recess or protrusion which may extend in the direction of the movement of the drive slider 40 on the bottom wall 432. That is, on the surface of the drive slider 40 contacting with the lock component 35, along the direction of the movement of the drive slider 40 on the bottom wall 432, the thickness of at least one portion of the drive slider 40 may be smaller than the thickness of at least another portion of the drive slider 40, and the transition surface may be provided between the at least one portion with a smaller thickness and the at least another portion with a larger thickness.

In these embodiments, the drive assembly of the lock device 30 may further include a lock component return spring (not shown in the drawings). When the drive slider 40 moves on the bottom wall 432 such that the contact position of the lock component 35 with the drive slider 40 is moved from the locations in the drive slider 40 with a larger thickness to the locations with a smaller thickness, the lock component return spring may provide restoring force for the lock component 35 such that the lock component 35 moves away from the guide bar 32, bringing the lock threaded area 351 on the lock component 35 to disengage from the outer threaded area 321 on the guide bar 32, thereby unlocking the lock device 30. In these embodiments, the lock component return spring may be connected to the lock component 35 at one end, and to the holder 31 or the carriage 43 at the other end. In some embodiment, the lock component return spring may be a tension spring or compression spring.

In these embodiments, other structures may be same as or similar to those of any one of the embodiments aforementioned and will not be described in detail.

In these embodiments, in ways which are same as or similar to those of any one of the embodiments aforementioned, the drive slider 40 may be pulled by the drive device 42 or pushed by the pushrod to move on the bottom wall 432 of the carriage 43, bringing the contact position of the lock component 35 with the drive slider 40 to be moved from the locations in the drive slider 40 with a smaller thickness through the transition surface to the locations with a larger thickness, thereby pushing the lock component 35 to move toward the guide bar 32 in the slide 311 (the second slide 3112) such that at least a portion of the threads on the lock threaded area 351 of the lock component 35 engage with at least a portion of the threads on the outer threaded area 321 of the guide bar 32 and lock the guide bar 32. When the guide bar 32 needs to be unlocked, the force applied on the drive device 42 or the pushrod may be removed, thus under the action of the restoring force provided by the slider return spring 41, the drive slider 40 may be moved in the direction opposite to the direction of the movement of the drive slider 40 during the lock process, while the lock component return mechanism may drive the lock component 35 to move toward the drive slider 40 (i.e., away from the guide bar 32) in the slide 311 (the second slide 3112), such that the contact position of the lock component 35 with the drive slider 40 is moved from the locations in the drive slider 40 with a larger thickness through the transition surface to the locations with a smaller thickness. Thus, the at least a portion of the threads on the lock threaded area 351 of the lock component 35 may be disengaged from the at least a portion of the threads on the outer threaded area 321 of the guide bar 32, thereby unlocking the guide bar 32.

In other embodiments of the present disclosure, the drive assembly also may not include the slider return spring 41 and the movement of the drive slider 40 may be completely controlled by the drive device 42. For example, the drive device 42 may be a rigid rod by which the drive slider 40 may be pushed and/or pulled.

In other embodiments of the present disclosure, the drive assembly also may not include the carriage 43. Rather, the drive slider 40 may be directly connected to the holder 31 and may be moved on the holder 31 with respect to the holder 31. For example, a slide rail or track may be provided on the holder 31. The drive slider 40 may be arranged on and moved along the slide rail or the track. A surface of the drive slider 40 may contact with the lock component 35 or the lock component drive block 39.

The drive device may be connected to the drive slider 40 at one end. On the surface of the drive slider 40 contacting with the lock component 35 or the lock component drive block 39, along the direction of the movement of the drive slider 40 on the holder 31, the thickness of at least one portion of the drive slider 40 may be smaller than at least another portion of the drive slider 40, and the transition surface may be provided between the at least one portion with a smaller thickness and the at least another portion with a larger thickness.

In these embodiments, other structures may be same as or similar to those of the embodiments aforementioned.

It will be understood that in some embodiments of the present disclosure, the drive assembly of the lock device 30 also may use any other suitable structures, as long as it is able to drive the lock component 35 to move toward and away from the guide bar 32 such that at least a portion of the threads on the lock threaded area 351 of the lock component 35 can engage with and disengage from at least a portion of the threads on the outer threaded area 321 of the guide bar 32.

Figure 11:
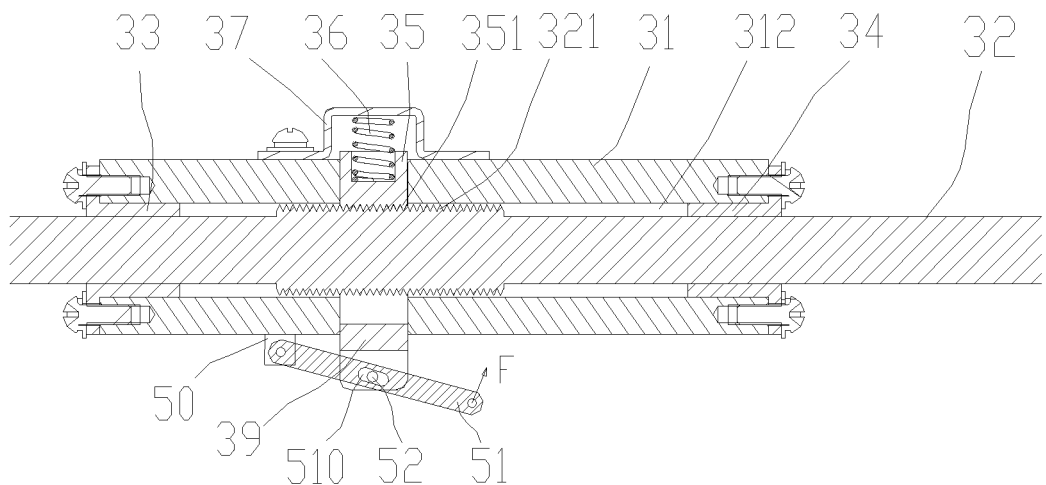
FIG. 11 is a schematic cross-sectional view of a lock device according to an embodiment of the present disclosure.

For example, in some embodiments of the present disclosure, the drive assembly of the lock device 30 may include a base 50 and a drive rod 51. The base 50 may be connected to the holder 31. The drive rod 51 may be slidably and rotatably connected to the lock component 35. For example, as shown in FIG. 11, the drive rod 51 may be provided with a slot 510. A pin 52 may pass through the slot 510 and be connected to the lock component 35. The drive rod 51 is able to slide and rotate with respect to the pin 52 received in the slot 510. One end of the drive rod 51 may be rotatably connected to the base 50. Thus, by applying a force at the other end of the drive rod 51 (for example, the force represented by the arrow F or the force in the opposite direction), the lock component 35 may be driven to move toward or away from the guide bar 32 via rotating the drive rod 51.

In addition, in some embodiments of the present disclosure, a lock component drive block 39 which is same as or similar to that of the embodiments aforementioned may be included. The drive rod 51 may be slidably and rotatably connected to the lock component drive block 39. The lock component drive block 39 may be driven by the drive rod 51; in turn the lock component 35 may be driven by the lock component drive block 39.

For example, in some embodiments, the drive assembly of the lock device 30 may include the lock component drive block 39, the base 50 and the drive rod 51.

The lock component drive block 39 may be received in the slide 311 and may move in the slide 311 in the extension direction of the slide 311 with respect to the holder 31. At least a portion of the lock component drive block 39 may contact with the lock component 35 and a passage 390 may be formed between the lock component drive block 39 and the lock component 35. The guide bar 32 may pass through the passage 390.

The base 50 may be connected to the holder 31. The drive rod 51 may be slidably and rotatably connected to the lock component drive block 39. For example, as shown in FIG. 11, the drive rod 51 may be provided with the slot 510. The pin 52 may pass through the slot 510 and be connected to the lock component drive block 39. The drive rod 51 is able to slide and rotate with respect to the pin 52 received in the slot 510. One end of the drive rod 51 may be rotatably connected to the base 50. Thus, by applying a force at the other end of the drive rod 51 (for example, the force represented by the arrow F or the force in the opposite direction), the lock component 35 may be driven to move toward or away from the guide bar 32 via rotating the drive rod 51. Therefore, the lock component drive block 39 may drive the lock component 35 to move toward or away from the guide bar 32.

In some embodiments, a return spring may further be included. For example, the end of the slide 311 facing toward the drive assembly may be open and the other end may be closed to form a bottom of the slide 311. The lock assembly may further include the return spring 36. The return spring 36 may be received in the slide 311. One end of the return spring 36 may abut against the bottom of the slide 311 and the other end against the lock component 35.

Or, in some embodiments, the slide 311 may run through the holder 31. The lock assembly may further include the return spring 36 and the return spring press plate 37. The return spring press plate 37 may be connected to the holder 31. One end of the return spring 36 may abut against the return spring press plate 37 and the other end against the lock component 35.

In some embodiments, the pin 52 may be a separated element, or also may be integrated with the lock component 35 or the lock component drive block 39.

In some embodiments, the drive rod 51 may be slidably or rotatably connected to the lock component 35 or the lock component drive block 39 in any other suitable ways.

Figure 12:
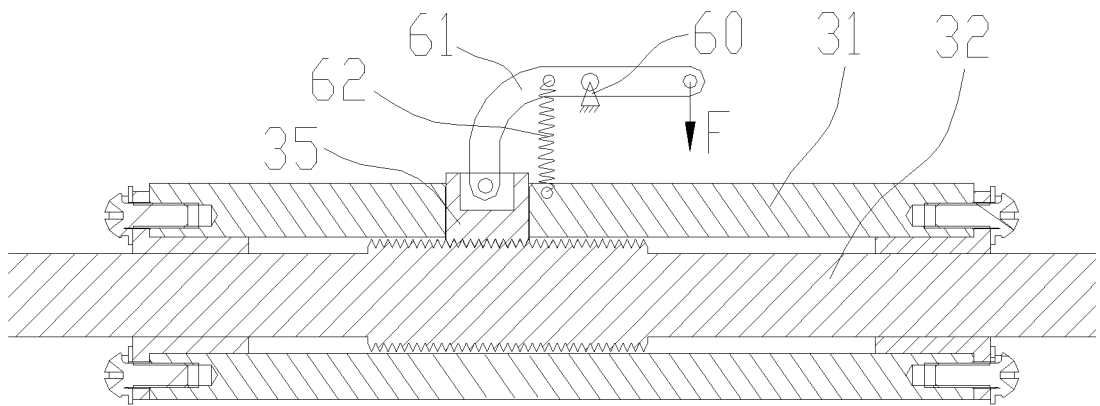
FIG. 12 is a schematic cross-sectional view of a lock device according to an embodiment of the present disclosure.

For example, in some embodiments of the present disclosure, the drive assembly of the lock device 30 may include a base 60, a drive rod 61 and a restoring spring 62. The drive rod 61 may be rotatably connected to the base 60. The base 60 may be connected to the holder 31 or other suitable location on the support arm 3. One end of the drive rod 61 may be rotatably connected to the lock component 35. One end of the restoring spring 62 may be connected to the drive rod 61 and the other end to the holder 31. Thus, by applying a force at the other end of the drive rod 61 (for example, the force represented by the arrow F in FIG. 12 or the force in the opposite direction), the lock component 35 may be driven to move toward or away from the guide bar 32. When this force is removed, the drive rod 61 and therefore the lock component 35 may be driven to go back to the original position through the stretching force or compression force of the restoring spring 62. One of these embodiments is shown in FIG. 12.

In addition, in other embodiments, a lock component drive block which is same as or similar to that of the embodiments aforementioned may be included. The drive rod 61 may be rotatably connected to the lock component drive block 39. The lock component drive block 39 may be driven by the drive rod 51; in turn the lock component 35 may be driven by the lock component drive block 39.

For example, in some embodiments, the drive assembly of the lock device 30 may include the lock component drive block 39, the base 60, the drive rod 61 and the restoring spring 62.

The lock component drive block 39 may be received in the slide 311 and may move in the slide 311 in the extension direction of the slide 311 with respect to the holder 31. At least a portion of the lock component drive block 39 may contact with the lock component 35 and a passage 390 may be formed between the lock component drive block 39 and the lock component 35. The guide bar 32 may pass through the passage 390.

The drive rod 61 may be rotatably connected to the base 60. The base 60 may be connected to the holder 31 or also may be arranged at another suitable location on the support arm 3. One end of the drive rod 61 may be rotatably connected to the lock component drive block 39. One end of the restoring spring 62 may be connected to the drive rod 61 and the other end to the holder 31. Thus, by applying a force at the other end of the drive rod 61 (for example, the force represented by the arrow F in FIG. 12 or the force in the opposite direction), the lock component drive block 39 may be driven to move toward or away from the guide bar 32. When this force is removed, the drive rod 61 and therefore the lock component drive block 39 may be driven to go back to the original position through the stretching force or compression force of the restoring spring 62.

In some embodiments, a return spring may further be included. For example, the end of the slide 311 facing toward the drive assembly may be open and the other end may be closed to form a bottom of the slide 311. The lock assembly may further include the return spring 36. The return spring 36 may be received in the slide 311. One end of the return spring 36 may abut against the bottom of the slide 311 and the other end against the lock component 35.

Or, in some embodiments, the slide 311 may run through the holder 31. The lock assembly may further include the return spring 36 and the return spring press plate 37. The return spring press plate 37 may be connected to the holder 31. One end of the return spring 36 may abut against the return spring press plate 37 and the other end against the lock component 35.

In these embodiments, the restoring spring 62 may be a tension spring or compression spring. The restoring spring 62 may be connected to the drive rod 61 at either side of the base 60.

In some embodiments of the present disclosure, the variety of spring mentioned above (for example, the return spring, the slider return spring, the lock component return spring, etc.) may be a compression spring, disc spring, tension spring, leaf spring, torsion spring or any other suitable elastic element (such as, rubber, etc.) by which the restoring force and its direction may be obtained and controlled.

In the embodiments of the present disclosure, the guide bar may be locked by the engagement of the threads on the lock threaded area of the lock component of the lock device with the outer threads on the outer threaded area of the guide bar. When the threads are engaged with each other, a locking in the longitudinal direction of the guide bar may be obtained. Even if a large force in the axial direction of the guide bar is applied, the threads will not be disengaged. During operation, each thread (or each pitch) may correspond to a locking position. The lock devices according to the embodiments of present disclosure are simple, easy to maintain, low cost, and not prone to failure, with high reliability and ability to bear a very large load. In addition, the lock device will not generate noise and need not be operated with electricity, and therefore operation is more convenient.

Although the present disclosure has been described through specific embodiments, the present disclosure is not limited to the specific embodiments described above. Those of skill in the art should understand that various modifications, alternatives and variations may be made based on the present disclosure, which all should be within the scope of protection of the present disclosure. Furthermore, "a (an) embodiment" or "another embodiment" mentioned above may represent different embodiments, or may also be combined completely or partly in one embodiment.

What is claimed is:

1. A lock device, comprising:
   a holder which is provided with a through hole running through the holder, wherein the holder is further provided with a slide, and the slide intersects with the through hole;
   a guide bar which is provided with an outer threaded area, wherein the guide bar passes through the through hole and the outer threaded area is located where the through hole intersects with the slide;
   a lock assembly comprising a lock component, wherein the lock component is received in the slide and is able to move in the slide, one end of the lock component facing toward the guide bar is provided with a lock threaded area, and the lock threaded area is able to engage with the outer threaded area; and
   a drive assembly that locks the lock device by driving the lock component to move toward the guide bar in the slide so as to engage at least a portion of threads on the lock threaded area of the lock component with at least a portion of outer threads on the outer threaded area of the guide bar; wherein the drive assembly unlocks the lock device by driving the lock component to move away from the guide bar in the slide so as to disengage the threads on the lock threaded area of the lock component from the outer threads on the outer threaded area of the guide bar.

2. The lock device of claim 1, wherein the drive assembly comprises:
   a drive slider connected to the holder and able to move on the holder with respect to the holder, wherein one surface of the drive slider contacts with the lock component; and
   a drive device, one end of which is connected to the drive slider;
   wherein, on the surface of the drive slider contacting with the lock component, along a direction of movement of the drive slider on the holder, a thickness of at least one portion of the drive slider is smaller than a thickness of at least another portion of the drive slider, and a transition surface is provided between the at least one portion with smaller thickness and the at least another portion with larger thickness.

3. The lock device of claim 2, wherein the drive assembly further comprises a lock component return spring, and one end of the lock component return spring is connected to the lock component and the other end of the lock component return spring is connected to the holder.

4. The lock device of claim 1, wherein the drive assembly comprises:
   a carriage comprising a bottom wall and at least one sidewall extending from the bottom wall in a direction angled with respect to the bottom wall, wherein a receiving space is formed between the bottom wall and the holder;
   a drive slider slidably received in the receiving space, wherein one surface of the drive slider rests on the bottom wall and another surface of the drive slider contacts with the lock component, and the drive slider is able to move on the bottom wall; and
   a drive device, one end of which is connected to the drive slider;
   wherein, on the another surface of the drive slider contacting with the lock component, along a direction of movement of the drive slider on the bottom wall, a thickness of at least one portion of the drive slider is smaller than a thickness of at least another portion of the drive slider, and a transition surface is provided between the at least one portion with smaller thickness and the at least another portion with larger thickness.

5. The lock device of claim 4, wherein the drive assembly further comprises a slider return spring, and one end of the slider return spring is connected to the at least one sidewall and the other end of the slider return spring is connected to the drive slider.

6. The lock device of claim 1, wherein the drive assembly comprises:
   a lock component drive block which is received in the slide and is able to move in the slide in an extension direction of the slide with respect to the holder, wherein at least a portion of the lock component drive block is able to contact with the lock component and a passage is formed between the lock component drive block and the lock component, and the guide bar passes through the passage;
   a drive slider which is connected to the holder and is able to move on the holder with respect to the holder; wherein one surface of the drive slider contacts with the lock component drive block; and
   a drive device, one end of which is connected to the drive slider;
   wherein, on the surface of the drive slider contacting with the lock component drive block, along a direction of movement of the drive slider on the holder, a thickness of at least one portion of the drive slider is smaller than a thickness of at least another portion of the drive slider, and a transition surface is provided between the at least one portion with smaller thickness and the at least another portion with larger thickness.

7. The lock device of claim 1, wherein the drive assembly comprises:
- a lock component drive block which is received in the slide and is able to move in the slide in an extension direction of the slide with respect to the holder, wherein at least a portion of the lock component drive block is able to contact with the lock component and a passage is formed between the lock component drive block and the lock component, and the guide bar passes through the passage;
- a carriage comprising a bottom wall and at least one sidewall extending from the bottom wall in a direction angled with respect to the bottom wall, wherein the carriage is connected to the holder and is located above the slide, and a receiving space is formed between the bottom wall and the holder;
- a drive slider slidably received in the receiving space, wherein one surface of the drive slider rests on the bottom wall and another surface of the drive slider contacts with the lock component drive block, and the drive slider is able to move on the bottom wall; and
- a drive device, one end of which is connected to the drive slider;
- wherein, on the another surface of the drive slider contacting with the lock component drive block, along a direction of movement of the drive slider on the bottom wall, a thickness of at least one portion of the drive slider is smaller than a thickness of at least another portion of the drive slider, and a transition surface is provided between the at least one portion with smaller thickness and the at least another portion with larger thickness.

8. The lock device of claim 7, wherein the drive assembly further comprises a slider return spring, and one end of the slider return spring is connected to the at least one sidewall and the other end of the slider return spring is connected to the drive slider.

9. The lock device of claim 1, wherein the drive assembly comprises:
- a base which is connected to the holder; and
- a drive rod which is slidably and rotatably connected to the lock component, wherein one end of the drive rod is rotatably connected to the base.

10. The lock device of claim 9, wherein the drive assembly further comprises a pin, the drive rod is provided with a slot, the pin passes through the slot and is connected to the lock component, and the drive rod is able to slide and rotate with respect to the pin.

11. The lock device of claim 1, wherein the drive assembly comprises:
- a lock component drive block which is received in the slide and is able to move in the slide in an extension direction of the slide with respect to the holder, wherein at least a portion of the lock component drive block is able to contact with the lock component and a passage is formed between the lock component drive block and the lock component, and the guide bar passes through the passage;
- a base which is connected to the holder; and
- a drive rod which is slidably and rotatably connected to the lock component drive block, wherein one end of the drive rod is rotatably connected to the base.

12. The lock device of claim 11, wherein the drive assembly further comprises a pin, the drive rod is provided with a slot, the pin passes through the slot and is connected to the lock component drive block, and the drive rod is able to slide and rotate with respect to the pin.

13. The lock device of claim 1, wherein the drive assembly comprises:
- a base;
- a drive rod rotatably connected to the base, wherein one end of the drive rod is rotatably connected to the lock component; and
- a restoring spring, wherein one end of the restoring spring is connected to the drive rod and the other end of the restoring spring is connected to the holder.

14. The lock device of claim 1, wherein the drive assembly comprises:
- a lock component drive block which is received in the slide and is able to move in the slide in an extension direction of the slide with respect to the holder, wherein at least a portion of the lock component drive block is able to contact with the lock component and a passage is formed between the lock component drive block and the lock component, and the guide bar passes through the passage;
- a base;
- a drive rod rotatably connected to the base, wherein one end of the drive rod is rotatably connected to the lock component drive block; and
- a restoring spring, wherein one end of the restoring spring is connected to the drive rod and the other end of the restoring spring is connected to the holder.

15. The lock device of claim 1, wherein one end of the slide facing toward the drive assembly is open and the other end of the slide is closed to form a bottom of the slide, the lock assembly further comprises:
- a return spring received in the slide, wherein one end of the return spring abuts against the bottom of the slide and the other end of the return spring abuts against the lock component.

16. The lock device of claim 1, wherein the slide runs through the holder, and the lock assembly further comprises:
- a return spring; and
- a return spring press plate connected to the holder;
- wherein one end of the return spring abuts against the return spring press plate and the other end of the return spring abuts against the lock component.

17. The lock device of claim 1, further comprising a support seat, one end of which is connected to the holder.

18. A lock device, comprising:
- a holder which is provided with a through hole running through the holder, wherein the holder is further provided with a slide, and the slide intersects with the through hole;
- a guide bar which is provided with an outer threaded area, wherein the guide bar passes through the through hole and the outer threaded area is located where the through hole intersects with the slide;
- a lock assembly comprising a lock component, wherein the lock component is received in the slide and is able to move in the slide, one end of the lock component facing toward the guide bar is provided with a lock threaded area, and the lock threaded area is able to engage with the outer threaded area; and
- a drive assembly which drives the lock component to move toward or away from the guide bar in the slide to lock or unlock the lock device, wherein the drive assembly comprises:
  - a drive slider connected to the holder and able to move on the holder with respect to the holder, wherein one surface of the drive slider contacts with the lock component; and a drive device, one end of which is connected to the drive slider;

wherein, on the surface of the drive slider contacting with the lock component, along a direction of movement of the drive slider on the holder, a thickness of at least one portion of the drive slider is smaller than a thickness of at least another portion of the drive slider, and a transition surface is provided between the at least one portion with smaller thickness and the at least another portion with larger thickness.

19. A lock device, comprising:

a holder which is provided with a through hole running through the holder, wherein the holder is further provided with a slide, and the slide intersects with the through hole;

a guide bar which is provided with an outer threaded area, wherein the guide bar passes through the through hole and the outer threaded area is located where the through hole intersects with the slide;

a lock assembly comprising a lock component, wherein the lock component is received in the slide and is able to move in the slide, one end of the lock component facing toward the guide bar is provided with a lock threaded area, and the lock threaded area is able to engage with the outer threaded area; and a drive assembly which drives the lock component to move toward or away from the guide bar in the slide to lock or unlock the lock device, wherein the drive assembly comprises:

a carriage comprising a bottom wall and at least one sidewall extending from the bottom wall in a direction angled with respect to the bottom wall, wherein a receiving space is formed between the bottom wall and the holder;

a drive slider slidably received in the receiving space, wherein one surface of the drive slider rests on the bottom wall and another surface of the drive slider contacts with the lock component, and the drive slider is able to move on the bottom wall; and a drive device, one end of which is connected to the drive slider;

wherein, on the another surface of the drive slider contacting with the lock component, along a direction of movement of the drive slider on the bottom wall, a thickness of at least one portion of the drive slider is smaller than a thickness of at least another portion of the drive slider, and a transition surface is provided between the at least one portion with smaller thickness and the at least another portion with larger thickness.

* * * * *